United States Patent [19]

Casals

[11] 4,133,879
[45] Jan. 9, 1979

[54] PROCESS FOR PRODUCING STABLE SOLUTIONS OF A SULPHONAMIDE AND A POTENTIATOR

[75] Inventor: Jose B. Casals, Roskilde, Denmark

[73] Assignee: Aktieselskabet Rosco, Tastrup, Denmark

[21] Appl. No.: 764,244

[22] Filed: Jan. 31, 1977

[30] Foreign Application Priority Data

Feb. 6, 1976 [DK] Denmark ............................... 497/76

[51] Int. Cl.$^2$ .................. A61K 31/625; A61K 31/505
[52] U.S. Cl. ...................................... 424/229; 424/251
[58] Field of Search ........................ 424/228, 229, 251

[56] References Cited

U.S. PATENT DOCUMENTS

| 3,551,564 | 12/1970 | Klaui et al. | 424/229 |
| 3,985,876 | 10/1976 | Hazlett et al. | 424/228 |
| 4,031,214 | 6/1977 | Easterbrook | 424/228 |
| 4,041,160 | 8/1977 | Stolar | 424/228 |

*Primary Examiner*—Jerome D. Goldberg
*Attorney, Agent, or Firm*—Lawrence Rosen; E. Janet Berry

[57] ABSTRACT

A process for the production of limpid and stable injectable preparations containing a sulphonamide and a potentiator is described, in which a diethanolamine salt of the sulphonamide and a salt of the potentiator are separately dissolved and the solutions mixed, the solvent mixture containing between 10 and 50% of water, between 15 and 30% of propyleneglycol, and between 20 and 40% of N-methylpyrrolidone, and the pH of the preparation being from 5.5 to 7.5.

5 Claims, No Drawings

PROCESS FOR PRODUCING STABLE SOLUTIONS OF A SULPHONAMIDE AND A POTENTIATOR

The present invention relates to injectable preparations containing a sulphonamide and a potentiator of the type 2,4-diamino-pyrimidines, and the production thereof.

The potentiator enhances the therapeutic effect of the sulphonamide.

As compounds of special value among potentiators may be mentioned diaveridine (2,4-diamino-5-(3,4-dimethoxybenzyl)-pyrimidine) and trimethoprim (2,4-diamino-5-(3,4,5-trimethoxybenzyl)-pyrimidine).

A preferred sulphonamide for use according to the invention is sulfafurazole (3,4-dimethyl-5-sulfanilamidoisoxazole) as the diethanolamine salt.

The sulphonamides form in water soluble salts with certain bases, whereas the potentiators form in water soluble salts only with certain acids. Therefore, by mixing aqueous solutions of the two components, a precipitation takes place, which is why the production in this way of injectable compositions has been considered impossible.

The present invention is based upon the surprising observation that stable injectable preparations can be produced if the potentiator is present in the form of the lactate and the sulphonamide in the form of the diethanolamine salt, when the pH-value is within the neutral range.

Other methods for the production of injectable sulphonamide-potentiator-solutions are known. Thus, the British Pat. No. 1,176,395 relates to the production of solutions, in which the sulphonamide as an alkalimetal salt is dissolved in water, and the potentiator is dissolved in a water-miscible organic solvent, after which the two solutions are united. The use of an alkalimetal salt of the sulphonamide results in a strongly basic reaction, which means that the preparation is irritating to the tissues at the injection site. If the pH is adjusted to a milder reaction (neutral), a precipitation of the preparation takes place.

Another method for the production of an injectable preparation of the said components is known from the Danish Pat. No. 128,229, describing the production of a suspension having a pH between 9.75 and 12.0. This is an undesirably high pH, and the preparation cannot, for example, be used for intravenous injection.

Finally, the published German Specification No. 2,445,400 describes a preparation consisting of sulfadimidine, sulfathiazole, and trimethoprim dissolved in N,N-dimethyl acetamide. Thus, this publication represents an attempt to avoid precipitation by using two different sulphonamides to obtain the desired sulphonamide concentration. However, owing to the low water content, approximately 15% in the resulting solution, the osmotic pressure will be high which is undesirable for injection purposes.

According to the present invention, the said disadvantages are encountered, and a stable, injectable sulphonamide-potentiator-solution is obtained, when the diethanolamine salt of a sulphonamide and the lactate of diaveridine or trimethoprim are dissolved in a mixture of water, propyleneglycol, and N-methylpyrrolidone, the water content being from 10-50% w/v, the propyleneglycol content 15-30% w/v, and the N-methylpyrrolidone content 20-40% w/v, and the pH of the preparation being 5.5-7.5. The reaction of such solution against the tissue fluids of the injected animals will substantially be neutral.

The preferred sulphonamide is sulfafurazole, but the invention is not thus limited, because other sulphonamides, which can form diethanolamine salts of sufficient solubility in the said mixture, can also be used.

Correspondingly, the preferred salt of the potentiator is the lactate, but other salts, such as the citrate or the hydrochloride, can also be used.

The ratio between sulphonamide and potentiator may vary within wide limits, viz. between 20:1 and 1:1. Clinically, the ratio 5:1 is mostly used.

Solutions according to the invention are easily produced by dissolving the potentiator in lactic acid and adding N-methylpyrrolidone, whereas the diethanolamine salt of the sulphonamide in a separate vessel is dissolved in a mixture of water and propyleneglycol, and finally the two solutions are mixed.

The contents of the active components in the preparation can be varied between 6 and 40% w/v, and are preferred to be between 12 and 36% w/v, the water content varying between 10 and 50% w/v, preferably 20-40% w/v.

The relatively high water content of the mixed solvents aids in reducing tissue damage at the injection site after intramuscular injection.

In the following, the process of the invention will be illustrated by some Examples.

EXAMPLE 1

In a beaker, containing 5 g of lactic acid and 10 ml of water, 4 g of diaveridine are dissolved, and then 30 ml of N-methylpyrrolidone are added with stirring at room temperature.

In another beaker, 20 g of sulfafurazole and 8.3 g of diethanolamine are dissolved in a mixture of 20 ml of water and 20 ml of propyleneglycol by heating to 60° C., and when the solution is limpid, it is cooled to room temperature.

The former solution is slowly poured into the solution containing the sulphonamide, and the pH is adjusted to 6.7-7.0. Then 1 ml of phenylcarbinol is added, and the volume of the solution is adjusted with propyleneglycol to make 100 ml. Finally, the solution is subjected to sterile filtration, and the filtrate is filled into sterile vials.

EXAMPLE 2

15 g of polyvinylpyrrolidone (average molecular weight 12,000) are dissolved in 60 ml of water. To 20 ml of this solution and 8 g of lactic acid in a beaker are added 8 g of trimethoprim, which is totally dissolved, and then 50 ml of N-methylpyrrolidone are added.

In another beaker, 40 g of sulfafurazole and 16.0 g of diethanolamine are dissolved in a mixture of 50 ml of polyvinylpyrrolidone solution and 40 ml of propyleneglycol by heating to 60° C., the solution being cooled to room temperature when limpid. The solution containing trimethoprim is slowly poured into the solution containing the sulphonamide, and pH is adjusted to 6.6-6.8. Then, 2 ml of phenylcarbinol are added, and the volume of the solution is adjusted to 200 ml with propyleneglycol. Finally, the solution is subjected to sterile filtration, and the filtrate is filled into sterile vials.

What is claimed is:

1. A stable, injectable preparation, comprising a therapeutically effective amount of a solution of the diethanolamine salt of sulfafurazole and a lactate or citrate of a potentiator for the sulphonamide, said potentiator being selected from the group consisting of diveridine and trimethoprim, and wherein the ratio of the diethanolamine salt of sulfafurazole to the potentiator is between 20:1 to 1:1, in a mixture of water, propyleneglycol, and N-methylpyrrolidone, the water content of the preparation being from 10 to 50% w/v, the propyleneglycol content from 15 to 30% w/v, and the N-methylpyrrolidone content from 20 to 40% w/v, and the pH of the preparation being 5.5 to 7.5.

2. The preparation of claim 1, in which the lactate of diaveridine is the potentiator.

3. The preparation of claim 1, in which the lactate of trimethoprim is the potentiator.

4. A process for the production of a preparation according to claim 1, which comprises separately preparing solutions of the sulfafurazole salt and the potentiator salt, each in a solvent or mixture of solvents selected from the group consisting of water, propyleneglycol, and N-methylpyrrolidone, uniting the solutions, and adjusting the pH to between 6.5 and 7.5.

5. A process according to claim 4, in which sulfafurazole and diethanolamine are dissolved in a mixture of equal amounts of water and propyleneglycol, and diaveridine is dissolved in an aqueous solution of lactic acid, and N-methylpyrrolidone is added, after which the two solutions are united, and the pH is adjusted to approximately 7.0.

* * * * *